US012569502B2

(12) United States Patent
Zi et al.

(10) Patent No.: US 12,569,502 B2
(45) Date of Patent: Mar. 10, 2026

(54) USE OF BILE ACIDS AND DERIVATIVES THEREOF IN PREPARATION OF GPR39 AGONIST

(71) Applicant: PEKING UNIVERSITY, Beijing (CN)

(72) Inventors: Zhentao Zi, Beijing (CN); Yi Xian, Beijing (CN); Shangchen Han, Beijing (CN); Enxing Zhou, Beijing (CN); Meihuang Wang, Beijing (CN); Yi Rao, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 939 days.

(21) Appl. No.: 17/772,952

(22) PCT Filed: Oct. 30, 2020

(86) PCT No.: PCT/CN2020/125307
§ 371 (c)(1),
(2) Date: Apr. 28, 2022

(87) PCT Pub. No.: WO2021/083336
PCT Pub. Date: May 6, 2021

(65) Prior Publication Data

US 2023/0091702 A1 Mar. 23, 2023

(30) Foreign Application Priority Data

Nov. 1, 2019 (WO) ................ PCT/CN2019/115038

(51) Int. Cl.
*A61K 31/575* (2006.01)
*A61K 33/30* (2006.01)

(52) U.S. Cl.
CPC ............ *A61K 31/575* (2013.01); *A61K 33/30* (2013.01)

(58) Field of Classification Search
CPC .......... A61K 31/575; A61K 33/30; A61P 1/00
See application file for complete search history.

(56) References Cited

U.S. PATENT DOCUMENTS 7,781,175 B2 * 8/2010 Fujii ........................ A61P 31/04 435/7.1
2010/0063018 A1 3/2010 Pellicciari et al.
2018/0148470 A1 5/2018 Li et al.

FOREIGN PATENT DOCUMENTS

CN 101395170 A 3/2009
EP 2 112 995 B1 7/2013
WO WO-2016173397 A1 * 11/2016 ................ A61P 1/00

OTHER PUBLICATIONS

Machine translation of WO 2016173397 (Year: 2016).*
(Continued)

*Primary Examiner* — Clinton A Brooks
*Assistant Examiner* — Izabela Schmidt
(74) *Attorney, Agent, or Firm* — Merchant & Gould P.C.; Daniel J. Pereira

(57) ABSTRACT

A use of the bile acids represented by Formula (1) and derivatives thereof in the preparation of a GPR39 agonist, as well as a drug composite which contains such bile acids and the derivatives thereof as the active ingredient, the drug composite being used to prevent, treat and/or relieve diseases associated with GPR39 activity.

Formula (I)

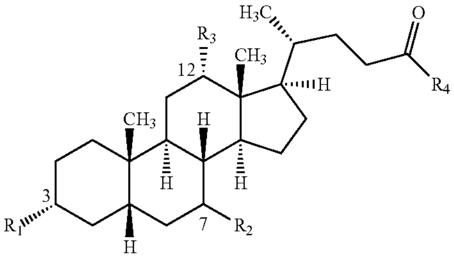

9 Claims, 6 Drawing Sheets

Specification includes a Sequence Listing.

(56) References Cited

OTHER PUBLICATIONS

Laxmi Sunuwar et al., Biochimica et Biophysica Acta (BBA)—Molecular Basis of Disease, vol. 1863, Issue 4, 2017, pp. 947-960. (Year: 2017).*
Hofmann AF et al., J Pediatr Gastroenterol Nutr. Nov. 2008;47(5):598-606. (Year: 2008).*
Brunel et al., Current Medicinal Chemistry, 2018, 25, 3613-3636 (Year: 2018).*
European Office Action issued Jan. 21, 2025, in European Patent Application No. 20 881 196.8.
European Supplementary Search Report issued Oct. 30, 2023, in European Patent Application No. 20 88 1196.
T.E. Adrian, et al., "Rectal taurocholate increases L cell and insulin secretion, and decreases blood glucose and food intake in obese type 2 diabetic volunteers," Diabetlogia (2012) 55: 2343-2347.
Sai Praneeth R. Bathena, et al., "The profile of bile acids and their sulfate metabolites in human urine and serum", Journal of Chromatography B, 942-943 (2013) 53-62.
Stuart Feldman, M.S., et al., "Effect of Bile Salts on Gastric Emptying and Intestinal Transit in the Rat", Gastroenterology, vol. 54, No. 5, May 1, 1968, pp. 918-921.
M. Hansen, et al., "Effect of chenodeoxycholic acid and the bile acid sequestrant colesevelam on glucagon-like peptide-1 secretion," Diabetes, Obesity and Metabolism, vol. 18, No. 6, pp. 571-580 (Mar. 22, 2016).
Alan F. Hofmann, et al., "Altered Bile Acid Metabolism in Childhood Functional Constipation: Inactivation of Secretory Bile Acids by Sulfation in a Subset of Patients," Journal of Pediatric Gastroenterology and Nutrition, vol. 47, No. 5, pp. 598-606 (Nov. 1, 2008).
Brian M. Moran, et al., "GPR39 receptors and actions of trace metals on pancreatic beta cell function and glucose homoeostasis," Acta Diabetologica, vol. 53, No. 2, Jun. 27, 2015, pp. 279-293.
Muneoka Satoshi, et al., "G protein-coupled receptor 39 plays an anti-inflammatory role by enhancing IL-10 production from macrophages under inflammatory conditions," vol. 834, Jul. 24, 2018, pp. 240-245.
Pia Steen Petersen, et al., "Deficiency of the GPR39 receptor is associated with obesity and altered adipocyte metabolism," vol. 25, No. 11, Jul. 22, 2011, pp. 3803-3814.
International Search report issued Feb. 3, 2021 in PCT/CN2020/125307, filed on Oct. 30, 2020, 4 pages.
Hershfinkel, "The Zinc Sensing Receptor, ZnR/GPR39, in Health and Disease", International Journal of Molecular Sciences, 2018, vol. 19, No. 439, pp. 1-19.

* cited by examiner

SEQUENCE LISTING

```
<160> NUMBER OF SEQ ID NOS: 16

<210> SEQ ID NO 1
<211> LENGTH: 39
<212> TYPE: DNA
<213> ORGANISM: Artificial Sequence
<220> FEATURE:
<223> OTHER INFORMATION: m39-H17A-F

<400> SEQUENCE: 1

tcccgtgtca tcgatgccag cgctgttcct gaatttgag                              39


<210> SEQ ID NO 2
<211> LENGTH: 22
<212> TYPE: DNA
<213> ORGANISM: Artificial Sequence
<220> FEATURE:
<223> OTHER INFORMATION: m39-H17A-R

<400> SEQUENCE: 2

atcgatgaca cgggagcaga tg                                                22


<210> SEQ ID NO 3
<211> LENGTH: 35
<212> TYPE: DNA
<213> ORGANISM: Artificial Sequence
<220> FEATURE:
<223> OTHER INFORMATION: m39-E90A-F

<400> SEQUENCE: 3

attggcatgc ccatggcgtt ctacagcatc atttg                                  35


<210> SEQ ID NO 4
<211> LENGTH: 25
<212> TYPE: DNA
<213> ORGANISM: Artificial Sequence
<220> FEATURE:
<223> OTHER INFORMATION: m39-E90A-R

<400> SEQUENCE: 4

catgggcatg ccaatcaaaa agacc                                             25


<210> SEQ ID NO 5
<211> LENGTH: 32
<212> TYPE: DNA
<213> ORGANISM: Artificial Sequence
<220> FEATURE:
<223> OTHER INFORMATION: m39-F115A-F
```

-continued

```
<400> SEQUENCE: 5

tccacacgtt cctcgctgag acgtgcagct ac                                32


<210> SEQ ID NO 6
<211> LENGTH: 25
<212> TYPE: DNA
<213> ORGANISM: Artificial Sequence
<220> FEATURE:
<223> OTHER INFORMATION: m39-F115A-R

<400> SEQUENCE: 6

gaggaacgtg tggagcttac aggac                                        25


<210> SEQ ID NO 7
<211> LENGTH: 33
<212> TYPE: DNA
<213> ORGANISM: Artificial Sequence
<220> FEATURE:
<223> OTHER INFORMATION: m39-E116A-F

<400> SEQUENCE: 7

cacacgttcc tctttgcgac gtgcagctac gcc                               33


<210> SEQ ID NO 8
<211> LENGTH: 25
<212> TYPE: DNA
<213> ORGANISM: Artificial Sequence
<220> FEATURE:
<223> OTHER INFORMATION: m39-E116A-R

<400> SEQUENCE: 8

aaagaggaac gtgtggagct tacag                                        25


<210> SEQ ID NO 9
<211> LENGTH: 32
<212> TYPE: DNA
<213> ORGANISM: Artificial Sequence
<220> FEATURE:
<223> OTHER INFORMATION: m39-D330A-F

<400> SEQUENCE: 9

tcctgccctt ctctgctacc ttcttctacc tc                                32


<210> SEQ ID NO 10
<211> LENGTH: 26
<212> TYPE: DNA
<213> ORGANISM: Artificial Sequence
<220> FEATURE:
<223> OTHER INFORMATION: m39-D330A-R

<400> SEQUENCE: 10

agagaagggc aggaggatca tgtatg                                       26


<210> SEQ ID NO 11
<211> LENGTH: 1371
<212> TYPE: DNA
<213> ORGANISM: Artificial Sequence
<220> FEATURE:
<223> OTHER INFORMATION: mouse GPR39 cDNA

<400> SEQUENCE: 11

atggcttcat ccagtggctc caaccacatc tgctcccgtg tcatcgatca cagccatgtt     60

cctgaatttg aggtggccac ttggatcaaa atcaccctca tcttggtgta cctgatcatc    120

tttgtggtag gcatcttggg caacagcgtc accatcaggg ttacgcaggt attgcagaag    180
```

-continued

```
aagggctatt tgcagaagga ggtgacagat cacatggtca gtttggcttg ttcagatatc    240

ttggtctttt tgattggcat gcccatggag ttctacagca tcatttggaa cccccctgacc    300

acacccagct atgctctgtc ctgtaagctc cacacgttcc tctttgagac gtgcagctac    360

gccacactgc tgcacgtgct gaccctcagc tttgagcgct acattgccat ttgtcatccc    420

ttcaagtata aagcagtgtc tggacctcgc caggtgaaac tgctgattgg ctttgtatgg    480

gtcacctccg ccctggtggc actgcctttg ctctttgcca tgggtatcga gtaccctctg    540

gtaaacgtac ccactcacaa gggactcaac tgcaacctct ctcgcacccg ccaccacgat    600

gaacctggaa actccaatat gtccatctgc acgaacctct ccaaccgttg ggaggtcttc    660

cagtccagca tctttggggc ctttgctgtt tacctggtgg tcctggcgtc tgtggctttc    720

atgtgttgga atatgatgaa agtgctaatg aagagcaagc agggcactct tgcagggacc    780

gggccacagc tccagctgag gaagtcagag agtgaggaga gccggacagc aagaagacag    840

accatcatat tcctgagact gattgtggtg acgttggccg tgtgttggat gcccaatcag    900

atccgacgga tcatggctgc agcaaaaccc aaacatgact ggaccagaac gtacttcagg    960

gcatacatga tcctcctgcc cttctctgat accttcttct acctcagctc tgtggtcaac   1020

cctctcctct acaacgtgtc ctctcagcag ttccggaagg tgttctggca ggtgctctgc   1080

tgccgcctga ctctgcagca tgccaaccaa gagaaacgcc agcgtgcccg cttcatctcc   1140

accaaggaca gcaccagctc agcccgcagc cccctcatct tcctagcctc ccggcgcagt   1200

aactcttcct ccaggagaac taacaaggtt ttcttaagca cttttcagac tgaggccaag   1260

cctggagagg ctaagcccca gcccttgagt cctgagtcac cacagactgg ctcagagacc   1320

aaaccagctg ggtccacccc agaaaatagt ttacaggagc aggaagtatg a             1371


<210> SEQ ID NO 12
<211> LENGTH: 21
<212> TYPE: DNA
<213> ORGANISM: Artificial Sequence
<220> FEATURE:
<223> OTHER INFORMATION: mGPR39-F

<400> SEQUENCE: 12

atggcttcat ccagtggctc c                                                21


<210> SEQ ID NO 13
<211> LENGTH: 31
<212> TYPE: DNA
<213> ORGANISM: Artificial Sequence
<220> FEATURE:
<223> OTHER INFORMATION: mGPR39-R

<400> SEQUENCE: 13

tcatacttcc tgctcctgta aactattttc t                                     31


<210> SEQ ID NO 14
<211> LENGTH: 1362
<212> TYPE: DNA
<213> ORGANISM: Artificial Sequence
<220> FEATURE:
<223> OTHER INFORMATION: human GPR39 cDNA

<400> SEQUENCE: 14

atggcttcac ccagcctccc gggcagtgac tgctcccaaa tcattgatca cagtcatgtc      60

cccgagtttg aggtggccac ctggatcaaa atcaccctta ttctggtgta cctgatcatc     120
```

-continued

```
ttcgtgatgg gccttctggg gaacagcgcc accattcggg tcacccaggt gctgcagaag    180

aaaggatact tgcagaagga ggtgacagac cacatggtga gtttggcttg ctcggacatc    240

ttggtgttcc tcatcggcat gcccatggag ttctacagca tcatctggaa tcccctgacc    300

acgtccagct acaccctgtc ctgcaagctg cacactttcc tcttcgaggc ctgcagctac    360

gctacgctgc tgcacgtgct gacactcagc tttgagcgct acatcgccat ctgtcacccc    420

ttcaggtaca aggctgtgtc gggaccttgc caggtgaagc tgctgattgg cttcgtctgg    480

gtcacctccg ccctggtggc actgcccttg ctgtttgcca tgggtactga gtaccccctg    540

gtgaacgtgc ccagccaccg gggtctcact tgcaaccgct ccagcacccg ccaccacgag    600

cagcccgaga cctccaatat gtccatctgt accaacctct ccagccgctg gaccgtgttc    660

cagtccagca tcttcggcgc cttcgtggtc tacctcgtgg tcctgctctc cgtagccttc    720

atgtgctgga acatgatgca ggtgctcatg aaaagccaga agggctcgct ggccgggggc    780

acgcggcctc cgcagctgag gaagtccgag agcgaagaga gcaggaccgc caggaggcag    840

accatcatct tcctgaggct gattgttgtg acattggccg tatgctggat gcccaaccag    900

attcggagga tcatggctgc ggccaaaccc aagcacgact ggacgaggtc ctacttccgg    960

gcgtacatga tcctcctccc cttctcggag acgtttttct acctcagctc ggtcatcaac   1020

ccgctcctgt acacggtgtc ctcgcagcag tttcggcggg tgttcgtgca ggtgctgtgc   1080

tgccgcctgt cgctgcagca cgccaaccac gagaagcgcc tgcgcgtaca tgcgcactcc   1140

accaccgaca gcgcccgctt tgtgcagcgc ccgttgctct tcgcgtcccg gcgccagtcc   1200

tctgcaagga gaactgagaa gattttctta agcacttttc agagcgaggc cgagccccag   1260

tctaagtccc agtcattgag tctcgagtca ctagagccca actcaggcgc gaaaccagcc   1320

aattctgctg cagagaatgg ttttcaggag catgaagttt ga                      1362


<210> SEQ ID NO 15
<211> LENGTH: 19
<212> TYPE: DNA
<213> ORGANISM: Artificial Sequence
<220> FEATURE:
<223> OTHER INFORMATION: hGPR39-F

<400> SEQUENCE: 15

atggcttcac ccagcctcc                                                   19


<210> SEQ ID NO 16
<211> LENGTH: 30
<212> TYPE: DNA
<213> ORGANISM: Artificial Sequence
<220> FEATURE:
<223> OTHER INFORMATION: hGPR39-R

<400> SEQUENCE: 16

tcaaacttca tgctcctgaa aaccattctc                                       30
```

USE OF BILE ACIDS AND DERIVATIVES THEREOF IN PREPARATION OF GPR39 AGONIST

CROSS-REFERENCE TO RELATED APPLICATIONS

The present application is a 35 U.S.C. § 371 national stage application of International patent application PCT/CN2020/125307, filed Oct. 30, 2020, which is based on and claims the benefit of priority to PCT/CN2019/115038, filed Nov. 1, 2019. The entire contents of these applications are incorporated herein by reference.

FIELD OF THE INVENTION

The present application relates to the field of biomedicine, and specifically to a use of a bile acid and a derivative thereof in the preparation of a GPR39 agonist.

BACKGROUND OF THE INVENTION

G Protein-Coupled Receptors (GPCRs) are a class of the most numerous membrane protein receptors in the human genome. This receptor family, having a seven-transmembrane structure with the N-terminus towards the outside of the cell and the C-terminus towards the cytoplasm, can be divided into five categories according to the sequence homology, which are glutamate receptor family (class C), rhodopsin receptor family (class A), adhesion receptor family, frizzled receptor family, and secretin receptor family, respectively. About 50% of the drugs currently on the market target GPCRs.

GPR39 is a kind of G protein-coupled receptor belonging to the ghrelin/neurotensin subfamily of the rhodopsin family (class A), which is mainly distributed in some areas of brain, pancreas, gastrointestinal tract, liver, kidney and other tissues and are involved in a variety of physiological processes. At present, the ligand of GPR39 is still unknown. Research has shown that zinc ions can activate GCP39 receptors by binding to histidines at positions 17 and 19 (H17&H19) in the N terminus of the extracellular domain.

Bile acids are steroidal natural products that can promote nutrient absorption. They are endogenous small molecules that regulate lipid and energy metabolism. They are synthesized by the liver and can be classified into primary bile acids and secondary bile acids depending on whether they are fermented by intestinal flora. In human, the primary bile acids are mainly cholic acid (CA) and chenodeoxycholic acid (CDCA), and the secondary bile acids mainly comprise lithocholic acid (LCA), deoxycholic acid (DCA) and ursodeoxycholic acid (UDCA), etc.

SUMMARY OF THE INVENTION

The present application provides a use of a bile acid and/or derivative thereof in the preparation of a GPR39 agonist.

In some embodiments, the bile acid and/or derivative thereof comprises a primary bile acid and derivative bile acid thereof, and the primary bile acid and/or derivative thereof is selected from the following group: CDCA, CA, and a derivative thereof.

In some embodiments, the bile acid and/or derivative thereof comprises secondary bile acid and/or derivative thereof, and the secondary bile acid and/or derivative thereof is selected from the following group: LCA, DCA, UDCA, and a derivative thereof.

In some embodiments, the bile acid and/or derivative thereof has a structure represented by Formula 1, Formula 1

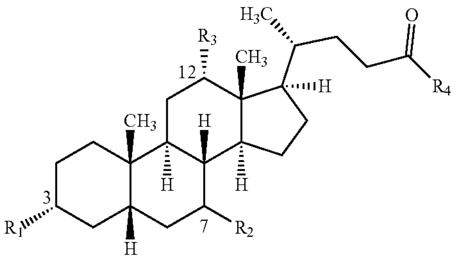

wherein, $R_1$ is HO or $OSO_3^-$;

$R_2$ is H or HO;

$R_3$ is H or HO;

$R_4$ is HO, taurine or glycine, or a pharmaceutically acceptable salt thereof.

In some embodiments, the $R_1$ is $OSO_3^-$.

In some embodiments, the $R_2$ is H.

In some embodiments, the $R_3$ is H.

In some embodiments, the $R_4$ is HO, taurine or glycine.

In some embodiments, the bile acid and/or derivative thereof is selected from the following group: TLCA, GLCA, LCAS, TLCAS, GLCAS, TDCA, GDCA, DCAS, TDCAS, GDCAS, GUDCA, TUDCA, UDCAS, TUDCAS, GUDCAS, GCDCA, TCDCA, CDCAS, TCDCAS, GCDCAS, TCA, GCA, CAS, TCAS, GCAS, and a derivative thereof.

In some embodiments, the bile acid and/or derivative thereof is selected from the following group: LCAS, TLCAS and GLCAS.

In some embodiments, the GPR39 agonist further comprises zinc ions.

In some embodiments, the concentration of the zinc ions is about 10 nM to about 10 μM.

In some embodiments, the bile acid and/or derivative thereof is capable of activating the GPR39 independent of a zinc ion binding site.

In some embodiments, the zinc ion binding sites comprise H17 and/or H19.

In some embodiments, the bile acid and/or derivative thereof is capable of activating the GPR39 independent of an activating site selected from the following group: E90, F115, E116 and D330.

In some embodiments, the GPR39 is human or mouse GPR39.

In another aspect, the present application also provides a use of the bile acid and/or derivative thereof in the preparation of a drug, the drug is used to prevent, treat and/or relieve a disease or disorder associated with GPR39 activity.

In some embodiments, the bile acid and/or derivative thereof comprises a primary bile acid and derivative bile acid thereof, and the primary bile acid and/or derivative thereof is selected from the following group: CDCA, CA, and a derivative thereof.

In some embodiments, the bile acid and/or derivative thereof comprises secondary bile acid and/or derivative thereof, and the secondary bile acid and/or derivative thereof is selected from the following group: LCA, DCA, UDCA, and a derivative thereof.

In some embodiments, the bile acid and/or derivative thereof has a structure represented by Formula 1, Formula 1

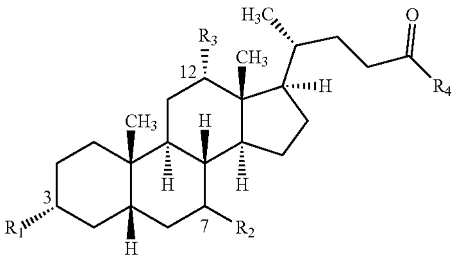

wherein, $R_1$ is HO or $OSO_3^-$;

$R_2$ is H or HO;

$R_3$ is H or HO;

$R_4$ is HO, taurine or glycine, or a pharmaceutically acceptable salt thereof.

In some embodiments, the $R_1$ is $OSO_3^-$.

In some embodiments, the $R_2$ is H.

In some embodiments, the $R_3$ is H.

In some embodiments, the $R_4$ is HO, taurine or glycine.

In some embodiments, the bile acid and/or derivative thereof is selected from the following group: TLCA, GLCA, LCAS, TLCAS, GLCAS, TDCA, GDCA, DCAS, TDCAS, GDCAS, GUDCA, TUDCA, UDCAS, TUDCAS, GUDCAS, GCDCA, TCDCA, CDCAS, TCDCAS, GCDCAS, TCA, GCA, CAS, TCAS, GCAS, and a derivative thereof.

In some embodiments, the bile acid and/or derivative thereof is selected from the following group: LCAS, TLCAS and GLCAS.

In some embodiments, the GPR39 agonist further comprises zinc ions.

In some embodiments, the concentration of the zinc ions is about 10 nM to about 10 μM.

In some embodiments, the bile acid and/or derivative thereof is capable of activating the GPR39 independent of a zinc ion binding site.

In some embodiments, the zinc ion binding sites comprise H17 and/or H19.

In some embodiments, the bile acid and/or derivative thereof is capable of activating the GPR39 independent of an activating site selected from the following group: E90, F115, E116 and D330.

In some embodiments, the GPR39 is human or mouse GPR39.

In another aspect, the present application provides a method for treating a disease or disorder associated with GPR39 activity, which comprises the following step: administering the bile acid and/or derivative thereof as described in the present application.

In another aspect, the present application provides a method for activating GPR39, which comprises the following step: administering the bile acid and/or derivative thereof as described in the present application.

In some embodiments, the method further comprises the following step: administering a zinc ion.

In another aspect, the present application provides a method for stimulating gastric emptying, which comprises the following step: administering the bile acid and/or derivative thereof as described in the present application.

In some embodiments, the bile acid and/or derivative thereof comprises a primary bile acid and derivative bile acid thereof, and the primary bile acid and/or derivative thereof is selected from the following group: CDCA, CA, and a derivative thereof.

In some embodiments, the bile acid and/or derivative thereof comprises secondary bile acid and/or derivative thereof, and the secondary bile acid and/or derivative thereof is selected from the following group: LCA, DCA, UDCA, and a derivative thereof.

In some embodiments, the bile acid and/or derivative thereof has a structure represented by Formula 1, Formula 1

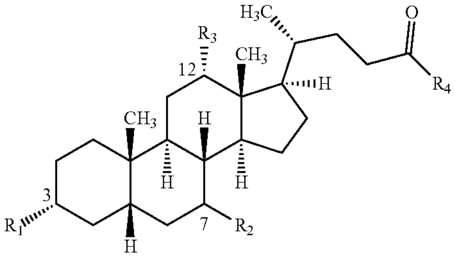

wherein, $R_1$ is HO or $OSO_3^-$;

$R_2$ is H or HO;

$R_3$ is H or HO;

$R_4$ is HO, taurine or glycine, or a pharmaceutically acceptable salt thereof.

In some embodiments, the $R_1$ is $OSO_3^-$.

In some embodiments, the $R_2$ is H.

In some embodiments, the $R_3$ is H.

In some embodiments, the $R_4$ is HO, taurine or glycine.

In some embodiments, the bile acid and/or derivative thereof is selected from the following group: TLCA, GLCA, LCAS, TLCAS, GLCAS, TDCA, GDCA, DCAS, TDCAS, GDCAS, GUDCA, TUDCA, UDCAS, TUDCAS, GUDCAS, GCDCA, TCDCA, CDCAS, TCDCAS, GCDCAS, TCA, GCA, CAS, TCAS, GCAS, and a derivative thereof.

In some embodiments, the bile acid and/or derivative thereof is selected from the following group: LCAS, TLCAS and GLCAS.

In some embodiments, the GPR39 agonist further comprises zinc ions.

In some embodiments, the concentration of the zinc ions is about 10 nM to about 10 μM.

In some embodiments, the bile acid and/or derivative thereof is capable of activating the GPR39 independent of a zinc ion binding site.

In some embodiments, the zinc ion binding sites comprise H17 and/or H19.

In some embodiments, the bile acid and/or derivative thereof is capable of activating the GPR39 independent of an activating site selected from the following group: E90, F115, E116 and D330.

In some embodiments, the GPR39 is human or mouse GPR39.

In another aspect, the present application also provides a drug composite for activating GPR39, which comprises the bile acid and/or derivative thereof as described in the present application, as well as a pharmaceutically acceptable carrier.

Those skilled in the art can easily perceive other aspects and advantages of the present application from the detailed description below. In the following detailed description, only exemplary embodiments of the present application are shown and described. As those skilled in the art will recognize, the content of the present application enables those skilled in the art to make changes to the disclosed specific embodiments without departing from the spirit and scope of the invention involved in the present application. Correspondingly, the drawings and descriptions in the specification of the present application are merely exemplary, rather than restrictive.

BRIEF DESCRIPTION OF THE DRAWINGS

The specific features of the invention involved in the present application are shown in the appended claims. The characteristics and advantages of the invention involved in the present application can be better understood by referring to the exemplary embodiments and the accompanying drawings described in detail below. A brief description of the drawings is as follows:

DETAILED DESCRIPTION OF THE EMBODIMENTS

Figure 1:
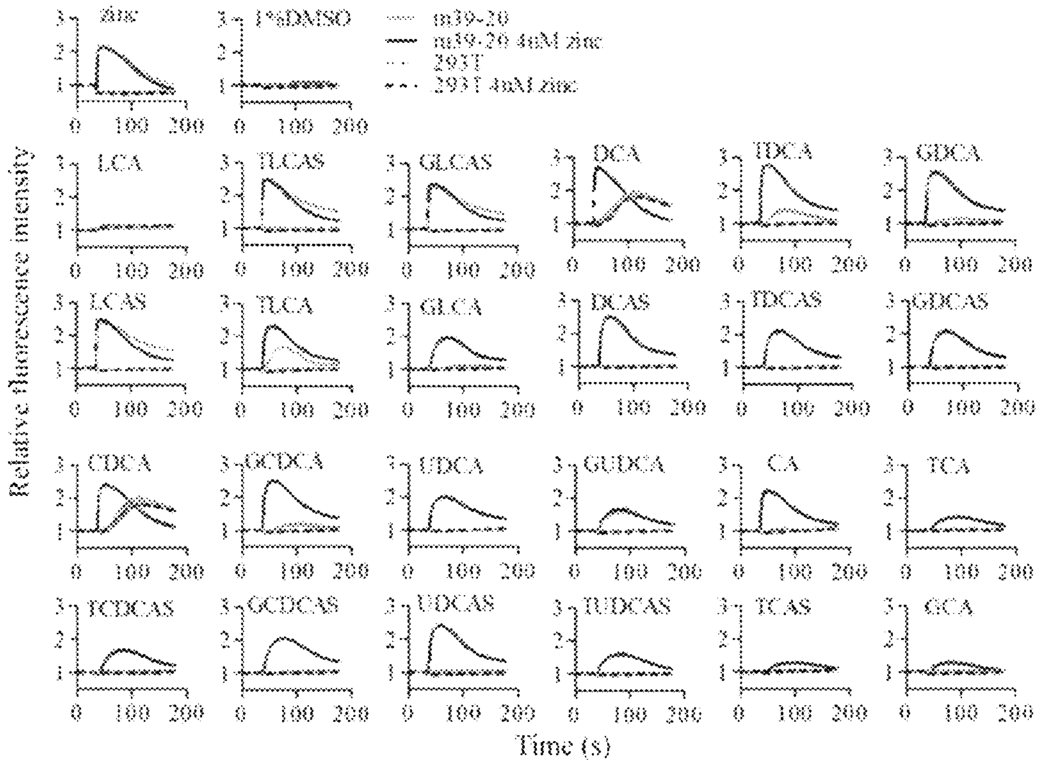
FIG. 1 shows the results of calcium imaging experiments on the activation of GPR39 receptor by the bile acids and derivatives thereof as described in the present application on m39-20 cell lines.

The implementation of the present application will be illustrated in the following specific examples, and other advantages and effects of the present application will be easily known by those familiar with this technology from the content disclosed in the specification.

In the present application, the term "receptor" generally refers to a class of special proteins found in the cell membrane or in the cell, which may specifically recognize and bind to extracellular signal molecules, thereby activating a series of physiological and biochemical reactions in the cell, so that the cell may produce corresponding effects in response to external stimuli. A receptor contains at least two functional domains: a ligand binding domain and an effector domain. According to its location, the receptor may be classified into membrane receptors and intracellular receptors. The term "ligand" generally refers to any molecules that bind to an anchoring protein. The ligands in an organism may usually be divided into two categories: simple inorganic small molecules or ions; and biomacromolecules, such as nucleic acids, proteins, polypeptides, etc.

In the present application, the term "GPCRs" generally refers to G protein coupled receptors (GPCRs), which is a collective term for the largest membrane protein receptors in the human genome, including about 800-1000 family members and accounting for about 3% of the entire genome. According to the sequence homology, they may be divided into five major categories, which are, respectively, glutamate receptor family (class C), rhodopsin receptor family (class A), adhesion receptor family, frizzled receptor family, and secretin receptor family. GPCRs are extensively distributed in tissues and cells, and play important roles in a variety of human physiological activities by mediating the conversion of extracellular stimuli into intracellular signals. GPCRs are very valuable drug targets. 30%-50% of therapeutic drugs currently used on the market exert their pharmacological effects through signaling pathways mediated by GPCRs.

In the present application, the term "GPR39" generally refers to G protein coupled receptor 39, which belongs to the ghrelin/neurotensin subfamily. Research has shown that, GPR39 is involved in gastrointestinal metabolism in human, and its endogenous ligands are zinc ions. GPR39 in other species may be all homologous proteins with sequence identity of not less than 50% obtained by comparison with human-derived GPR39 (NCBI Reference Sequence: NP_001499.1) or murine-derived GPR39 (NCBI Reference Sequence: NP_081953.2) using Clustal Omega sequence alignment software. Where, the sequence homology of human-derived and murine-derived GPR39 proteins is above 82%.

In the present application, the term "agonist" generally refers to substances capable of enhancing the activity of another molecule or other sites of a receptor. According to the source, the agonists may be divided into endogenous agonists and exogenous agonists. According to the efficacy, the agonists may be divided into full agonists, super agonists, partial agonists, and inverse agonists, and the like. Agonists are substances that may bind to receptors, change the status of the receptors and elicit biological responses to the receptors. In the present application, the GPR39 agonist refers to a substance capable of binding to the GPR39 receptor and enhancing its activities, for example, a bile acid and a derivative thereof, a zinc ion, known GPR39 agonists TC-G 1008 (Peukert et al, 2014) and TM-N 1324 (Frimurer et al, 2017).

In the present application, the term "bile acid" generally refers to a class of endogenous steroidal natural products composed of a rigid steroid skeleton with 1-3 hydroxyl groups and an alkane branch with a terminal carboxyl group, which is the main component of bile, accounting for 50%-60% of the total bile. Bile acid is mainly synthesized from cholesterol in the liver and secreted in the duodenum. About 40%-50% of the cholesterol in the human body is converted into bile acid. Bile acid Farnesoid receptor X (FXR) as well as pregnane X receptor (PXR) are currently known specific nuclear receptors for bile acid. Bile acid may regulate the absorption of fat and oil in food by human body and the synthesis of bile acid by activating FXR and PXR.

The basic structure of bile acid is 24-carbon carboxylic acid cholane series with cyclopentane polyhydrophenanthrene as the core, as represented by Formula 1. In the present application, $R_1$ may be HO or $OSO_3^-$; $R_2$ may be H or HO; $R_3$ may be H or HO; $R_4$ may be HO, taurine (CAS: 107-35-7) or glycine (CAS: 56-40-6). Where, in some embodiments, $OSO_3^-$ may bind protons; in other embodiments, $OSO_3^-$ may also bind other ions to form a salt. More than 90% of bile acid in the human body are present in conjugated forms. Bile acid binds to glycine or taurine through a peptide bond to form taurine-conjugated bile acid or glycine-conjugated bile acid. There are very few free bile acids.

Formula 1

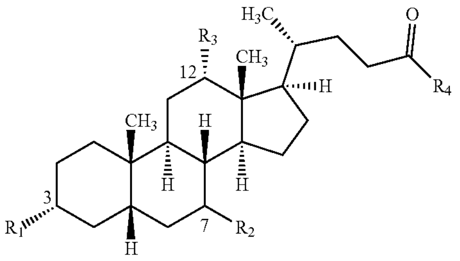

According to the source, the bile acid may be divided into two categories: a primary bile acid and a secondary bile acid. The bile acid directly synthesized from cholesterol in liver cells is called primary bile acid, including:

1) Cholic acid (CA, CAS: 81-25-4): $R_1$ is HO, $R_{2\alpha}$ is HO, $R_{2\beta}$ is H, $R_3$ is HO, $R_4$ is HO;
2) Chenodeoxycholic acid (CDCA, CAS: 474-25-9): $R_1$ is HO, $R_{2\alpha}$ is HO, $R_{2\beta}$ is H, $R_3$ is H, $R_4$ is HO.

The structures of cholic acid (CA) and chenodeoxycholic acid (UDCA) only differ in the different number of hydroxyl groups contained in the cholane skeleton, that is, cholic acid (CA) contains 3 hydroxyl groups (3α, 7α, 12α), while chenodeoxycholic acid contains 2 hydroxyl groups (3α, 7α).

Primary bile acid is subjected to bacterial action in the gut and generate a bile acid by dehydroxylation at the 7α position, which is called secondary bile acid, including:

1) Deoxycholic acid (DCA, CAS: 83-44-3): $R_1$ is HO, $R_{2\alpha}$ is H, $R_{2\beta}$ is H, $R_3$ is HO, $R_4$ is HO;
2) Lithocholic acid (LCA, CAS: 434-13-9): $R_1$ is HO, $R_{2\alpha}$ is H, $R_{2\beta}$ is H, $R_3$ is H, $R_4$ is HO;
3) Ursodeoxycholic acid (UDCA, CAS: 128-13-2): $R_1$ is HO, $R_{2\alpha}$ is H, $R_{2\beta}$ is HO, $R_3$ is H, $R_4$ is HO.

In the present application, the term "bile acid derivative" generally refers to a compound sharing a core four-membered ring structure with cholic acid (CA) and being substituted by various substituent groups.

In the present application, the derivative of cholic acid (CA) comprises:

1) TCA (CAS: 145-42-6): $R_1$ is HO, $R_{2\alpha}$ is HO, $R_{2\beta}$ is H, $R_3$ is HO, $R_4$ is taurine;
2) GCA (CAS: 863-57-0): $R_1$ is HO, $R_{2\alpha}$ is HO, $R_{2\beta}$ is H, $R_3$ is HO, $R_4$ is glycine;
3) TCAS (CAS: 67030-62-0): $R_1$ is $OSO_3^-$, $R_{2\alpha}$ is HO, $R_{2\beta}$ is H, $R_3$ is HO, $R_4$ is taurine.

In the present application, the derivative of chenodeoxycholic acid (CDCA) comprises:

1) GCDCA (CAS: 16564-43-5): $R_1$ is HO, $R_{2\alpha}$ is HO, $R_{2\beta}$ is H, $R_3$ is H, $R_4$ is glycine;
2) TCDCAS (CAS: 67030-59-5): $R_1$ is $OSO_3^-$, $R_{2\alpha}$ is HO, $R_{2\beta}$ is H, $R_3$ is H, $R_4$ is taurine;
3) GCDCAS (CAS: 66874-09-7): $R_1$ is $OSO_3^-$, $R_{2\alpha}$ is HO, $R_{2\beta}$ is H, $R_3$ is H, $R_4$ is glycine.

In the present application, the derivative of deoxycholic acid (DCA) comprises:

1) TDCA (CAS: 1180-95-6): $R_1$ is HO, $R_{2\alpha}$ is H, $R_{2\beta}$ is H, $R_3$ is HO, $R_4$ is taurine;
2) GDCA (CAS: 16409-34-0): $R_1$ is HO, $R_{2\alpha}$ is H, $R_{2\beta}$ is H, $R_3$ is HO, $R_4$ is glycine;
3) DCAS (CAS: 60237-35-6): $R_1$ is $OSO_3^-$, $R_{2\alpha}$ is H, $R_{2\beta}$ is H, $R_3$ is HO, $R_4$ is HO;
4) TDCAS (CAS: not available): $R_1$ is $OSO_3^-$, $R_{2\alpha}$ is H, $R_{2\beta}$ is H, $R_3$ is HO, $R_4$ is taurine;
5) GDCAS (CAS: 66874-09-7): $R_1$ is $OSO_3^-$, $R_{2\alpha}$ is H, $R_{2\beta}$ is H, $R_3$ is HO, $R_4$ is glycine.

In the present application, the derivative of lithocholic acid (LCA) comprises:

1) TLCA (CAS: 6042-32-6): $R_1$ is HO, $R_{2\alpha}$ is H, $R_{2\beta}$ is H, $R_3$ is H, $R_4$ is taurine;
2) GLCA (CAS: 24404-83-9): $R_1$ is HO, $R_{2\alpha}$ is H, $R_{2\beta}$ is H, $R_3$ is H, $R_4$ is glycine;
3) LCAS (CAS: 64936-81-8): $R_1$ is $OSO_3^-$, $R_{2\alpha}$ is H, $R_{2\beta}$ is H, $R_3$ is H, $R_4$ is HO;
4) TLCAS (CAS: 64936-83-0): $R_1$ is $OSO_3^-$, $R_{2\alpha}$ is H, $R_{2\beta}$ is H, $R_3$ is H, $R_4$ is taurine;
5) GLCAS (CAS: 64936-82-9): $R_1$ is $OSO_3^-$, $R_{2\alpha}$ is H, $R_{2\beta}$ is H, $R_3$ is H, $R_4$ is glycine.

In the present application, the derivative of ursodeoxycholic acid (UDCA) comprises:

1) GUDCA (CAS: 64480-66-6): $R_1$ is HO, $R_{2\alpha}$ is H, $R_{2\beta}$ is HO, $R_3$ is H, $R_4$ is glycine;
2) UDCAS (CAS: 68780-73-4): $R_1$ is $OSO_3^-$, $R_{2\alpha}$ is H, $R_{2\beta}$ is HO, $R_3$ is H, $R_4$ is HO;
3) TUDCAS (CAS: not available): $R_1$ is $OSO_3^-$, $R_{2\alpha}$ is H, $R_{2\beta}$ is HO, $R_3$ is H, $R_4$ is taurine.

In the present application, the "salt" in the term "pharmaceutically acceptable salt" refers to a product formed by ionic bonding with the bile acid, and the salt is generally prepared by reacting the bile acid and/or a derivative thereof with an acid or a base, wherein the acid or base is suitable for administering to the subjects. For example, the acid comprises, but not limited to, ammonium chloride, hydrochloric acid, sulfuric acid, phosphoric acid, acetic acid, citric acid, tartaric acid, ascorbic acid, benzoic acid, and common amino acids such as glycine, alanine, phenylalanine, arginine, etc; the base comprise, but not limited to, sodium carbonate, sodium bicarbonate, aqueous ammonia, ethanolamine, N-methylglucosamine, etc.

In the present application, the term "about" generally refers to varying in a range of 0.5%-10% above or below a specified value, for example, varying in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified value.

USE

In one aspect, the present application provides a use of a bile acid and/or derivative thereof in the preparation of a GPR39 agonist. The bile acid and/or derivative thereof comprises a primary bile acid and derivative bile acid thereof, a secondary bile acid and derivative bile acid thereof.

GPR39 is a G protein-coupled receptor, whose sequence is similar to those of the growth hormone secretagogue receptor (GHSR) and the neurotensin receptors 1 and 2

(NTSR1 and NTSR2). As inferred from bioinformatics, GPR39 protein is composed of 453 amino acid residues and contains seven transmembrane domains with characteristics of growth hormone secretagogue (GHSR). GPR39 is extensively distributed in tissues, such as brain tissue, stomach and small intestine, pancreas, thyroid and colon, etc.

In the present application, the GPR39 may be derived from mice, human and other species. The murine-derived GPR39 protein sequence may be determined according to NCBI Reference Sequence: NP_081953.2; the human-derived GPR39 protein sequence may be determined according to NCBI Reference Sequence: NP_001499.1; and the GPR39 protein sequences of other species are all homologous proteins with sequence identity of not less than 50% obtained by comparison with human-derived GPR39 or murine-derived GPR39 using Clustal Omega sequence alignment software. For example, the GPR39 proteins may be derived from pig, cattle, goat, rabbit or monkey. In the present application, the GPR39 may also be cell lines that stably express GPR39, e.g., murine-derived m39-20 cell lines, human-derived human GPR39-2 cell lines and cell lines of other species that may express GPR39. In the present application, the GPR39 may also be cultured cells that transiently overexpress human-derived or murine-derived GPR39 by transfecting 293T cells with lipofectamine3000 transfection kit (Invitrogen Co.).

In the present application, the bile acid and/or derivative thereof comprises a primary bile acid and derivative bile acid thereof, and the primary bile acid and/or derivative thereof may be selected from, but not limited to, the following group: CDCA, CA, and a derivative thereof. For example, the derivative of the primary bile acid may be a derivative of CA, e.g., TCA, GCA, TCAS; may be a derivative of CDCA, e.g., GCDCA, TCDCAS, GCDCAS; and may also be a derivative bile acid sharing a core four-membered ring structure with CA, CDCA and being substituted by a different group. The substituent group may be alkyl, alkenyl, alkynyl, halogen, trifluoromethyl, aryl, mercapto, cyano, alkoxy, etc.

The bile acid and/or derivative thereof comprises a secondary bile acid and/or derivative thereof, and the secondary bile acid and/or derivative thereof may be selected from, but not limited to, the following group: LCA, DCA, UDCA, and a derivative thereof. For example, the derivative of the secondary bile acid may be a derivative of LCA, e.g., TLCA, GLCA, LCAS, TLCAS, GLCAS; may be a derivative of DCA, e.g., TDCA, GDCA, DCAS, TDCAS, GDCAS; may be a derivative of UDCA, e.g., GUDCA, UDCAS, TUDCAS; and may also be a derivative bile acid sharing a core four-membered ring structure with LCA, DCA, UDCA and being substituted by a different group. The substituent group may be alkyl, alkenyl, alkynyl, halogen, trifluoromethyl, aryl, mercapto, cyano, alkoxy, etc.

Intracellular calcium imaging is a routine technique to study cell functions, the basic principle of which is to detect the concentration of the calcium ion in tissues or cells using a calcium indicator, thereby reflecting certain reactions in the tissues or cells. In the present application, the intracellular calcium released from a cell line that stably or transiently expresses GPR39 is detected using Fluo8-AM, a calcium fluorescent indicator, so as to determine the activation of the GPR39 receptor by the bile acid and derivative thereof.

For example, in murine-derived m39-20 cell lines stably expressing GPR39, TLCA, GLCA, LCAS, TLCAS, GLCAS, TDCA, GDCA, DCAS, TDCAS, GDCAS, GUDCA, UDCAS, TUDCAS, GCDCA, TCDCAS, GCDCAS, TCA, GCA, TCAS could elicit varying extents of intracellular calcium signals (FIG. 1); while in 293T cells not expressing GPR39, only DCA and CDCA may induce observable calcium signals, but other bile acid derivatives cannot induce calcium signals within 293T cells, indicating that the bile acid derivatives induce calcium signals within the cells by binding to and activating the GPR39 receptor.

Zinc Ions Positively Allosterically Modulate the Activation of GPR39 by a Bile Acid and Derivative Thereof In the present application, the GPR39 agonist further comprises zinc ions. $Zn^{2+}$ has been reported as the ligand of GPR39. By using $Zn^{2+}$ to stimulate a cell line that transiently or stably expresses GPR39, intracellular calcium release (Yasuda, Miyazaki et al, 2007), phosphoinositide accumulation (EC50=22 μM), as well as cAMP elevation (EC50=7.4 μM) (Holst, Egerod et al, 2007) may be detected. For example, zinc ions may bind to GPR39 and activate GPR39 in m39-20 cell lines, thereby inducing intracellular calcium signals (FIG. 1).

In the present application, the zinc ion binding sites comprise H17 and/or H19. Human-derived zinc ion binding sites H17 and H19 are determined according to NCBI Reference Sequence: NP_001499.1, which are histidine 17 and histidine 19 counted from the N-terminus of GPR39 protein sequence, respectively. And the GPR39 protein sequences of other species may be aligned with a reference sequence NP_001499.1 by using Clustal Omega sequence alignment software so as to obtain the corresponding H17 and H19 zinc ion binding sites. For example, the zinc ion binding sites corresponding to the murine-derived GPR39 protein are histidine 17 and histidine 19 counted from the N-terminus of the murine-derived GPR39 protein sequence.

In the present application, the bile acid and/or derivative thereof is capable of activating the GPR39 independent of a zinc ion binding site. For example, in some embodiments, murine-derived wild-type (WT) GPR39 or zinc ion binding site mutant (H17A and H19A) GPR39 are transiently expressed in 293T cells by using lipofectamine3000 transfection kit. The activation effect of LCAS on the wild-type (WT) and mutants (H17A and H19A) is detected by calcium imaging. The results show that LCAS may activate mutant (H17A and H19A) GPR39, thus inducing intracellular calcium signals, and its EC50 value is 24±0.8 μM, which is less than the EC50 value of LCAS activated wild-type (WT) GPR39 of 33.1±5.1 μM, indicating that bile acid and/or derivative thereof activate GPR39 independent of the zinc ion binding sites H17 and H19.

Allosteric modulation means that after a substance acts on a receptor protein, the spatial conformation of the receptor protein changes, which in turn causes the functional change of the receptor protein. The substance that may promote the signal transduction of the receptor protein is a positive allosteric modulator, whereas, the substance that inhibits the signal transduction of the receptor protein is a negative allosteric modulator. Allosteric modulation plays an important modulatory effect on the function of the receptor, but the specific mechanism of allosteric modulation is still unclear currently. It is generally considered that there are multiple sites on a receptor. When one site binds a ligand, the conformation of the receptor itself may change, which in turn affects the binding activity of other sites.

Figure 2:
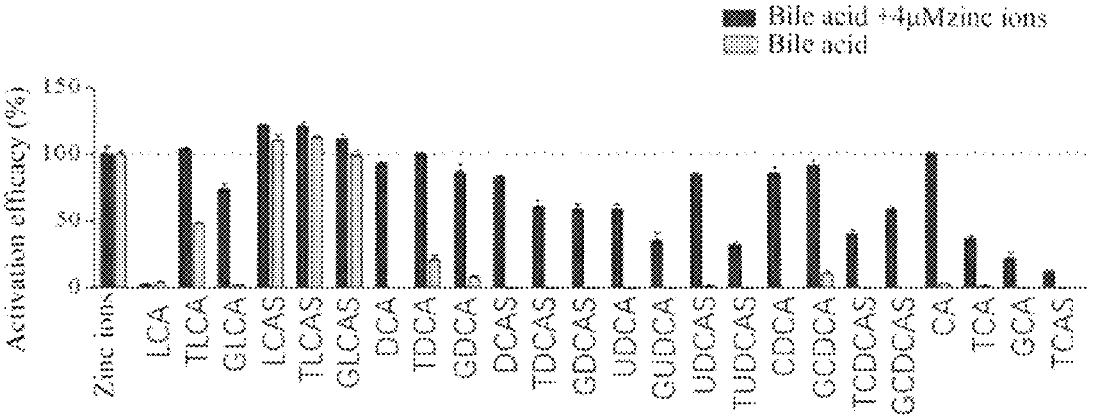
FIG. 2 shows a histogram of activation efficacy of the bile acids and derivatives thereof as described in the present application in the activation of GPR39 receptors on m39-20 cell lines.
Figure 3:
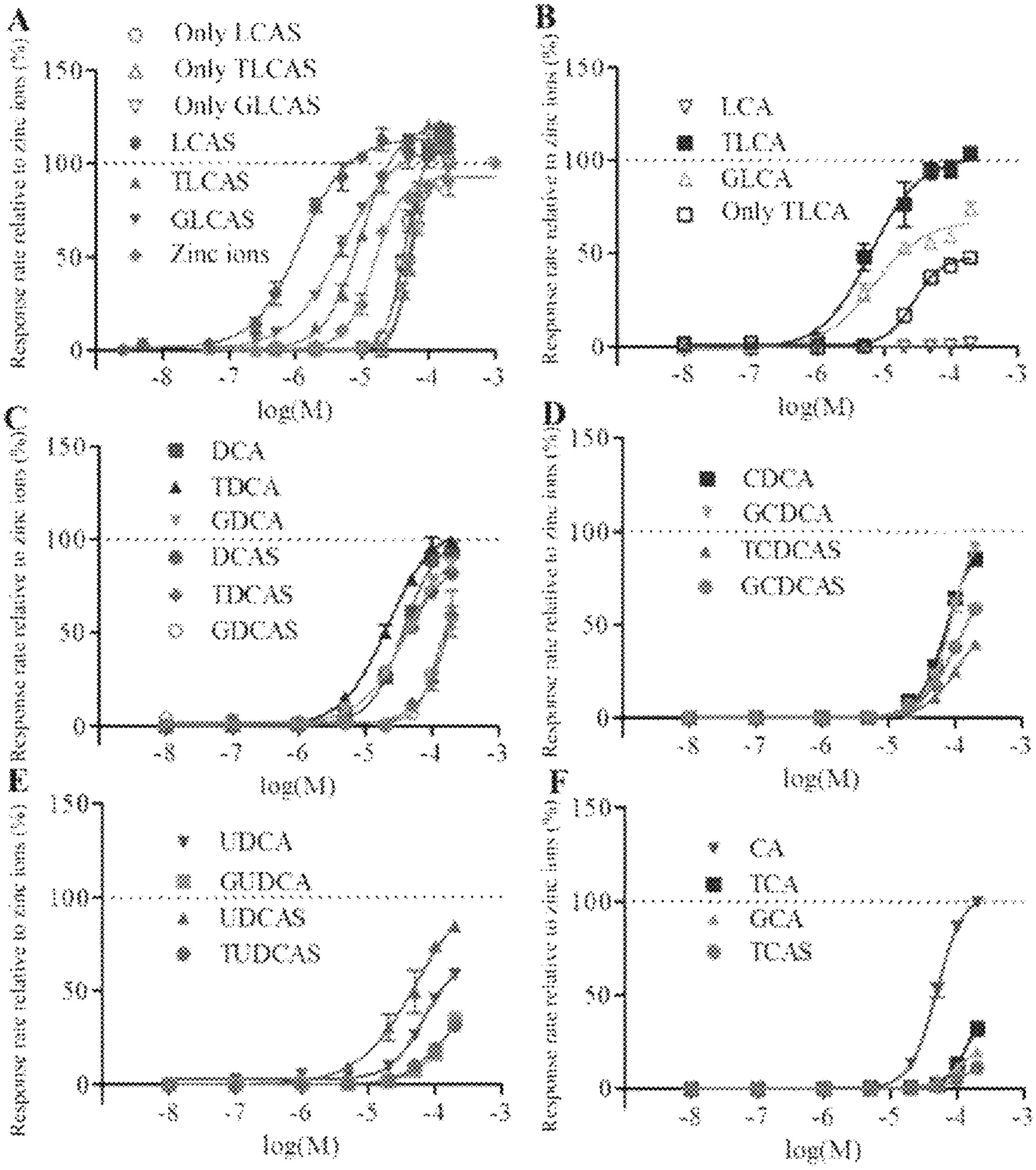
FIGS. 3A-3F show dose curves of the bile acids and derivatives thereof as described in the present application for activating GPR39 receptors on m39-20 cell lines.

EC50, that is, concentration for 50% of maximal effect, refers to the concentration at which 50% of the maximal effect may be caused. In the present application, EC50 refers to the concentration of a bile acid and derivative thereof as well as zinc ions that may cause 50% of the maximal effect on the GPR39 receptor. The activation efficacy represents the potency strength of the agonist. In some embodiments, after the addition of zinc ions, the activation efficacy of GLCA, TDCA, GDCA, DCAS, TDCAS, GDCAS, GUDCA, UDCAS, TUDCAS, GCDCA, TCDCAS, GCD-CAS, TCA, GCA, TCAS to activate GPR39 in murine-derived m39-20 cell lines all has been obviously improved (Table 1, FIG. 2), and the dose curve of the bile acid to activate the GPR39 receptor shifts to the left, indicating that zinc ions have a positive allosteric modulation effect on the activation of the GPR39 receptor by the bile acid and derivative thereof, where the concentration of the zinc ions may be 0.01 μM, 0.1 μM, 0.7 M, 3 μM, 20 μM. However, the activation efficacy of LCAS, TLCAS, GLCAS at a concentration of 200 μM to activate GPR39 in murine-derived m39-20 cell lines is higher than that of other bile acids and derivatives thereof before the addition of zinc ions, and the activation efficacy increases slightly after adding zinc ions, the reason for which may be that when the $R_1$ on the carbon at position 3 of the cholic acid molecule is $OSO_3^-$, the activation efficacy of LCA on GPR39 is higher.

In another aspect, the present application also provides a use of the bile acid and/or derivative thereof in the preparation of a drug, the drug is used to prevent, treat and/or relieve a disease or disorder associated with GPR39 activity. Because GPR39 is highly expressed in human jejunum, ileum, duodenum, stomach, liver, adipose tissue, retinal pigment epithelium and pituitarium and many other cells and tissues, it has become one of the targets for intervening drug action and has gained more and more attention. In the present application, the drug may be a drug composite containing a safe and effective dose of the bile acid and/or derivative thereof as described in the present application as well as a pharmaceutically acceptable carrier or excipient. The carrier comprises, but not limited to, saline, glucose, buffer, water, glycerin, ethanol and a combination thereof. The drug composite of the present application may be prepared into injections, tablets, capsules, pills and other forms. The excipient comprises, but not limited to, binder, filler, disintegrant, lubricant in tablets; wine, vinegar, drug juice, etc. in Chinese medicine pills; base part in semi-solid preparations such as ointment and cream; preservative, antioxidant, flavoring agent, fragrance, cosolvent, emulsifier, solubilizer, osmotic pressure regulator, colouring agent, etc. in liquid preparations.

Method

In another aspect, the present application also provides a method for treating a disease or disorder associated with GPR39 activity, which comprises the following step: administering the bile acid and/or derivative thereof as described in the present application. In some embodiments, a drug composite containing a safe and effective dose of the bile acid and/or derivative thereof as described in the present application as well as a pharmaceutically acceptable carrier or excipient may be administered by various different dosing routes, e.g., orally, subcutaneously, intravenous injection, intramuscular injection, inhalation, rectally and the like, to treat a disease or disorder associated with GPR39 activity.

In another aspect, the present application also provides a method for activating GPR39, which comprises the following step: administering the bile acid and/or derivative thereof as described in the present application. The subject of administration may be mammals, such as human, rats, mice; and it may also be isolated tissues, organs or cells, etc.

In another aspect, the present application also provides a method for stimulating gastric emptying, which comprises the following step: administering the bile acid and/or derivative thereof as described in the present application. In the present application, the term "gastric emptying" generally refers to a process of discharging food from the stomach into the duodenum. Research has shown that GPR39 is involved in gastrointestinal motility and secretion of digestive juice in the body. Therefore, the GPR39 receptor may become the acting target for treating gastrointestinal diseases, and these diseases usually affect gastric motility, such as functional dyspepsia, diabetic gastroparesis, gastric spasm; diseases caused by abnormal colorectal motility, such as irritable bowel syndrome, diarrhea, chronic constipation, etc.

In some embodiments, the bile acid and/or derivative thereof is capable of activating the GPR39 independent of an activating site selected from the following group: E90, F115, E116 and D330. In some embodiments, the bile acid may induce the intracellular calcium signals of mutants E90A, F115A, E116A and D330A of GPR39, indicating that the activation of GPR39 by the bile acid is independent of known agonist binding sites: E90, F115, E116 and D330. In addition, in some embodiments, the bile acid and/or derivative thereof may be independent of an activating site selected from the following group: E90, F115, E116 and E330. In some embodiments, the bile acid may induce the intracellular calcium signals of mutants E90A, F115A, E116A and E330A of GPR39, indicating that the activation of GPR39 by the bile acid is independent of known agonist binding sites: E90, F115, E116 and E330.

Without intending to be limited by any theory, the following examples are only intended to illustrate the bile acid and derivative thereof, the preparation method and the use of the present application, and are not intended to limit the scope of the present invention.

EXAMPLES

Example 1. Construction of Cell Lines m39-20 Stably Expressing Murine-Derived GPR39 Gene 1.1 Cell Culture Cells were cultured using DMEM medium (gibco), in which were added with 10% dialyzed fetal bovine serum (gibco), 100 U/mL of penicillin and streptomycin. The cells were cultured at 37° C. and 5% $CO_2$.

1.2 Construction of Lentiviral Vectors

Figure 11:
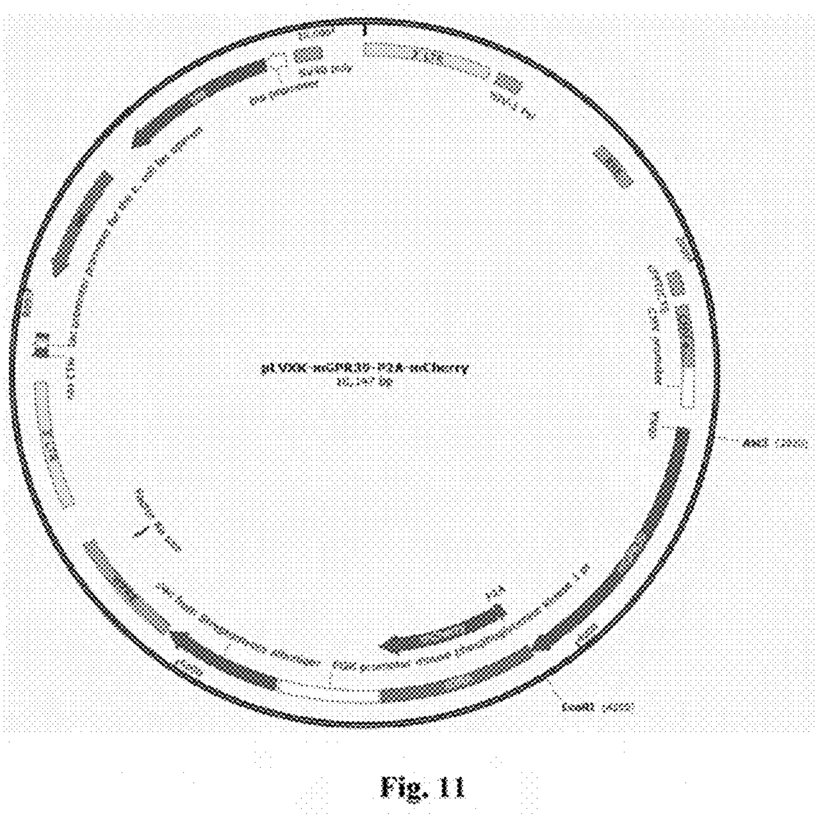
FIG. 11 shows a map of a lentiviral vector PLVXK-mGPR39-P2A-mCherry.

Primers mGPR39-F (whose sequence is as set forth in SEQ ID NO: 12) and mGPR39-R (whose sequence is as set forth in SEQ ID NO: 13) were used to amplify the target gene murine-derived GPR39 cDNA sequence (with the sequence as set forth in SEQ ID NO: 11) from the cDNA library of mouse duodenum. The obtained target sequence was cloned onto a lentiviral vector PLVXK-mGPR39-P2A-mCherry (see FIG. 11). The positive monoclones were verified by sequencing and then purified for use.

1.3 Cell Transfection and Puromycin Screening

HEK293T cells (purchased from ATCC) were seeded in a 6-well plate (coming Co.) at an appropriate density (about 0.5-2×$10^5$/well). When the cell density reached above 30%, the plasmid PLVXK-mGPR39-P2A-mCherry was transfected with Lipofectamine 3000 (Invitrogen) at a concentration of 2 μg per well. The cells were passaged 24 hours after transfection, the puromycin (gibco) was added into the medium at a concentration of 2 μg/mL for antibiotic screening of cells. After 2-4 days of continuous screening, the cells screened for puromycin resistance were trypsinized and screened by flow cytometry for monoclones with red fluorescence. And these monoclones were seeded in a 96-well plate and cultured in a medium without puromycin for around 10 days. Cell colonies with red fluorescence were sorted under a fluorescence microscope, trypsinized and then passaged and expanded in a 6-well plate. Cell lines m39-20 stably expressing murine-derived GPR39 were obtained through the above methods.

Example 2 FLIPR Calcium Imaging 2.1 Cell Culture

Before the experiment of calcium imaging, m39-20 cells of Example 1 were firstly seeded in a PDL-coated black-walled transparent-bottomed 96-well plate (coming Co.) at an appropriate density (about $3\times10^4$ cells/well), and cultured at 37° C. and 5% $CO_2$ for at least 24 hours, so that the cell density reached 90%-100%.

2.2 Preincubation of Cells with Calcium Dye

Calcium dye Fluo8-AM (ATT bioquest Co.) was dissolved in DMSO solvent to formulate a stock solution of 1 μg/μL. The resulting calcium dye stock solution was then diluted 500-fold with a 4K solution (NaCl 150 mM, KCl 4 mM, $MgCl_2$ 2 mM, $CaCl_2$ 2 mM, glucose 11 mM, HEPES 10 mM, pH=7.4), as a calcium dye working solution, which was added into m39-20 cells from Example 2.1 at 50 μL per well, and incubated at room temperature for 25 min. After then, the calcium dye working solution was replaced with the 4K solution (50 μL per well), and acclimated for 5 min at room temperature for the subsequent calcium imaging experiment.

2.3 FLIPR Calcium Imaging

Bile acids and derivatives thereof as listed in Table 1 below were dissolved in dimethyl sulfoxide (DMSO, Sigma Co.) solvent to formulate a stock solution of 50 mM, which was stored at −20° C. During calcium imaging with FLIPR, the drug was diluted with the above 4K solution into a working concentration of 400 μM, and packaged into another 96-well plate. The drug solution and the cell samples in Example 2.2 were placed into the designated position of the FLIPR instrument (MolecularDevices Co.) respectively. The instrument parameters were set so that 50 μL of the drug solution may be added into the culture wells within 2 s. The fluorescence recording result within the first 30 seconds was used as the baseline value. The FLIPR robot arm was programmed to automatically add bile acids and derivatives thereof into the cell sample culture wells at the 31st second. 1% of DMSO solvent was used as the blank control.

The results of FLIPR calcium imaging experiment of the bile acids and derivatives thereof are shown in FIG. 1, wherein the horizontal coordinate represents the time, and the vertical coordinate represents the relative fluorescence intensity. It may be known from the results of the calcium imaging experiment that: 1) LCAS, TLCAS, GLCAS may also induce a strong intracellular calcium signaling response in m39-20 cells in the absence of zinc ions, but the blank control group of 1% DMSO cannot induce observable calcium signals on m39-20 cells, indicating that the activation of the GPR39 receptor depends on the bile acids and derivatives thereof; 2) only DCA and CDCA may induce observable calcium signals on HEK293T cells, while other bile acids and derivatives thereof cannot induce observable calcium signals on 293T cells, indicating that the intracellular calcium signals induced by the bile acids and derivatives thereof depend on the GPR39 receptor.

2.4 Allosteric Modulation Experiment of Zinc Ions

Following the method in Example 2.2, cells were preincubated with calcium dye. After that, the calcium dye working solution was replaced with a 4K solution containing 4 μM zinc ions (50 μL per well), followed by acclimation for 5 min at room temperature. Following the method in Example 2.3, a solution of a bile acid and derivative thereof was formulated, into which were then added 4 μM zinc ions for the subsequent calcium imaging experiment, with the results shown in FIG. 1, in which the vertical coordinate represents the relative fluorescence intensity, and the horizontal coordinate represents the time. It may be known from the results of the calcium imaging experiment that: 1) in the presence of 4 μM zinc ions, a variety of bile acids and derivatives thereof may induce different degrees of intracellular calcium signal response in m39-20; 2) in the presence of 4 μM zinc ions, the calcium signals induced by DCA, CDCA on m39-20 cell lines were greatly different from the calcium signals induced by them on 293T cell lines, indicating that DCA, CDCA are capable of activating GPR39 receptors in the presence of zinc ions.

Formula I

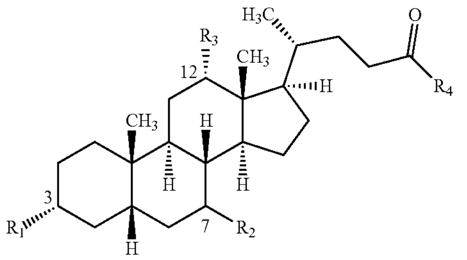

TABLE 1

| | | | | | | | | Only bile acid | | Bile acid + 4 μM zinc ions | |
|---|---|---|---|---|---|---|---|---|---|---|---|
| Type | Skeleton | Name | $R_1$ | $R_2$ (α) | $R_2$ (β) | $R_3$ | $R_4$ | EC50 (μM) | Efficacy (%) | EC50 (μM) | Efficacy (%) |
| Secondary bile acids | LCA | LCA | HO | H | H | H | HO | >>200 | 0 | >100 | 1.3 ± 1.1 |
| | | TLCA | | | | | Taurine | 44 ± 10 | 47.8 ± 1.1 | 8.1 ± 2.4 | 103.5 ± 1.1 |
| | | GLCA | | | | | Glycine | >>200 | 0 | 13.5 ± 3.4 | 74 ± 4.1 |
| | | LCAS | $OSO_3$ | | | | HO | 41 ± 4.5 | 111.1 ± 3.9 | 0.88 ± 0.16 | 120.8 ± 1.6 |
| | | TLCAS | | | | | Taurine | 71.6 ± 76. | 112.7 ± 1.3 | 9 ± 2.1 | 121 ± 2.9 |
| | | GLCAS | | | | | Glycine | 47.9 ± 9.4 | 98.8 ± 4.6 | 8 ± 1.8 | 110.8 ± 4.1 |
| | DCA | DCA | HO | H | H | H | HO | >>200 | 0 | 58.4 ± 10 | 93.1 ± 1.4 |
| | | TDCA | | | | O | Taurine | >200 | 22.8 ± 3 | 27.6 ± 7.1 | 99.3 ± 1.7 |
| | | GDCA | | | | | Glycine | >200 | 7.7 ± 1.7 | 46 ± 10.3 | 86.4 ± 6.3 |
| | | DCAS | $OSO_3$ | | | | HO | >>200 | 0 | 37.8 ± 1 | 81.9 ± 2.2 |
| | | TDCAS | | | | | Taurine | >>200 | 0 | >100 | 60.1 ± 5.5 |
| | | GDCAS | | | | | Glycine | >>200 | 0 | >100 | 58.5 ± 4.8 |

TABLE 1-continued

| Type | Skeleton | Name | $R_1$ | $R_2$ (α) | $R_2$ (β) | $R_3$ | $R_4$ | Only bile acid EC50 (μM) | Only bile acid Efficacy (%) | Bile acid + 4 μM zinc ions EC50 (μM) | Bile acid + 4 μM zinc ions Efficacy (%) |
|---|---|---|---|---|---|---|---|---|---|---|---|
| | UDCA | UDCA | HO | H | H | H | HO | >>200 | 0 | >100 | 58.5 ± 4 |
| | | GUDCA | | | O | | Taurine | >>200 | 0 | >100 | 35.3 ± 6.8 |
| | | UDCAS | $OSO_3$ | | | | HO | >>200 | 0 | 68.6 ± 16.3 | 84.7 ± 2.4 |
| | | TUDCAS | | | | | Glycine | >>200 | 0 | >100 | 31.4 ± 3.2 |
| Primary bile acids | CDCA | CDCA | HO | HO | H | H | HO | >>200 | 0 | 75.1 ± 7.6 | 85 ± 5.2 |
| | | GCDCA | | | | | Glycine | >200 | 16.5 ± 2.4 | 80.6 ± 3.6 | 91.2 ± 4.4 |
| | | TCDCAS | $OSO_3$ | | | | Taurine | >>200 | 0 | >100 | 39.7 ± 3.3 |
| | | GCDCAS | | | | | Glycine | >>200 | 0 | >100 | 58.6 ± 2 |
| | CA | CA | HO | HO | H | HO | HO | >>200 | 0 | 49.2 ± 3.3 | 99.3 ± 2.1 |
| | | TCA | | | | | Taurine | >>200 | 0 | >100 | 31.8 ± 3 |
| | | GCA | | | | | Glycine | >>200 | 0 | >100 | 20 ± 2.7 |
| | | TLCAS | OSO3 | | | | Taurine | >>200 | 0 | >100 | 11.4 ± 1.6 |

Example 3 Detection of Concentration for 50% of Maximal Effect (EC50) and Activation Efficacy The concentration for 50% of maximal effect (EC50) and the activation efficacy of bile acids and derivatives thereof to activate GPR39 receptors on m39-20 cell lines were detected using FLIPR, respectively, with the detection results being summarized in Table 1 above. The histogram of activation efficacy of bile acids and derivatives thereof to activate GPR39 receptors was shown in FIG. 2, and the dose curves were shown in FIGS. 3A-3F. The results show that bile acids and derivatives thereof have a dose effect on the activation of GPR39 receptors, in which LCAS, TLCAS, GLCAS have the strongest activation capacity, and zinc ions may shift the dose curve of GPR39 activation by bile acids and derivatives thereof to the left, indicating that zinc ions have a positive allosteric modulation effect on the activation of GPR39 by bile acids and derivatives thereof.

Example 4 Positive Allosteric Modulation of Bile Acid-Activated GPR39 Receptors by Different Concentrations of Zinc Ions Take LCAS as an example, the effects of adding different concentrations of zinc ions on the concentration for 50% of maximal effect (EC50) to activate GPR39 receptors on m39-20 cell lines were detected respectively according to the method of Example 3, with the detection results being summarized in Table 2 below, and the dose curve being shown in FIG. 4A. The results show that: 1) when the concentration of zinc ions is less than 0.1 μM, the positive allosteric modulation effect of zinc ions disappears; 2) when the concentration of zinc ions is more than 1 μM, the positive allosteric modulation capacity on GPR39 is more obvious.

TABLE 2

| Zinc ions (μM) | EC50 (μM) |
|---|---|
| 4 | 0.7 ± 0.03 |
| 2 | 1.9 ± 0.03 |
| 1 | 6.4 ± 0.67 |
| 0.4 | 20.1 ± 0.67 |
| 0.2 | 25.4 ± 1.1 |
| 0.1 | 30.6 ± 2 |
| 0.05 | 30.7 ± 2.4 |
| 0 | 31 ± 2.1 |

Figure 5:
FIG. 5 shows a map of the pCMV6-3HA-mGPR39 (H17A&H19A)-P2A-mCherry plasmid as described in the present application.

Example 5 Bile Acids Activate Mutants of GPR39, H17A and H19A 5.1 Construction of Site-Directed Mutant Vector The pCMV6-3HA-mGPR39-P2A-mCherry vector carrying murine-derived GPR39 gene and having a total length of about 7 Kbp was selected as the PCR template, and a site-directed mutant vector was obtained by PCR site-directed mutagenesis. With the mutation site as the centre, a forward primer m39-H17A-F and a reverse primer m39-H17A-R were designed by extending approximately 15 bp each way, which sequences were respectively shown in Table 3 below. At 1 bp upstream of the mutation site, a 15 bp complementary sequence to the forward primer was designed, and the length of the reverse primer was designed to maintain the annealing temperature of the primer at 60° C. A high-fidelity DNA polymerase (Phanta Max Super-fidelity DNA polymerase, Vazyme) was used for site-directed PCR. 5 μL cutsmart buffer (NEB) and 1 μL restriction endonuclease DpnI (NEB) were added into the PCR product for overnight digestion, and then 10 μL of the product was transferred into 50 μL DH5α for heat shock transformation. The corresponding resistant solid LB medium was selected to coat and culture the product and enable it grow overnight at 37° C. A single colony was picked for inoculation, and the bacteria were shaken to extract the plasmid which was verified by sequencing. A monoclonal vector which had been sequenced to be correct was selected and marked as pCMV6-3HA-mGPR39(H17A&H19A)-P2A-mCherry, which structure was shown in FIG. 5.

TABLE 3

| Name | SEQ ID NO |
|---|---|
| m39-H17A-F | 1 |
| m39-H17A-R | 2 |

5.2 Transiently Transfected Cell System

Figure 4:
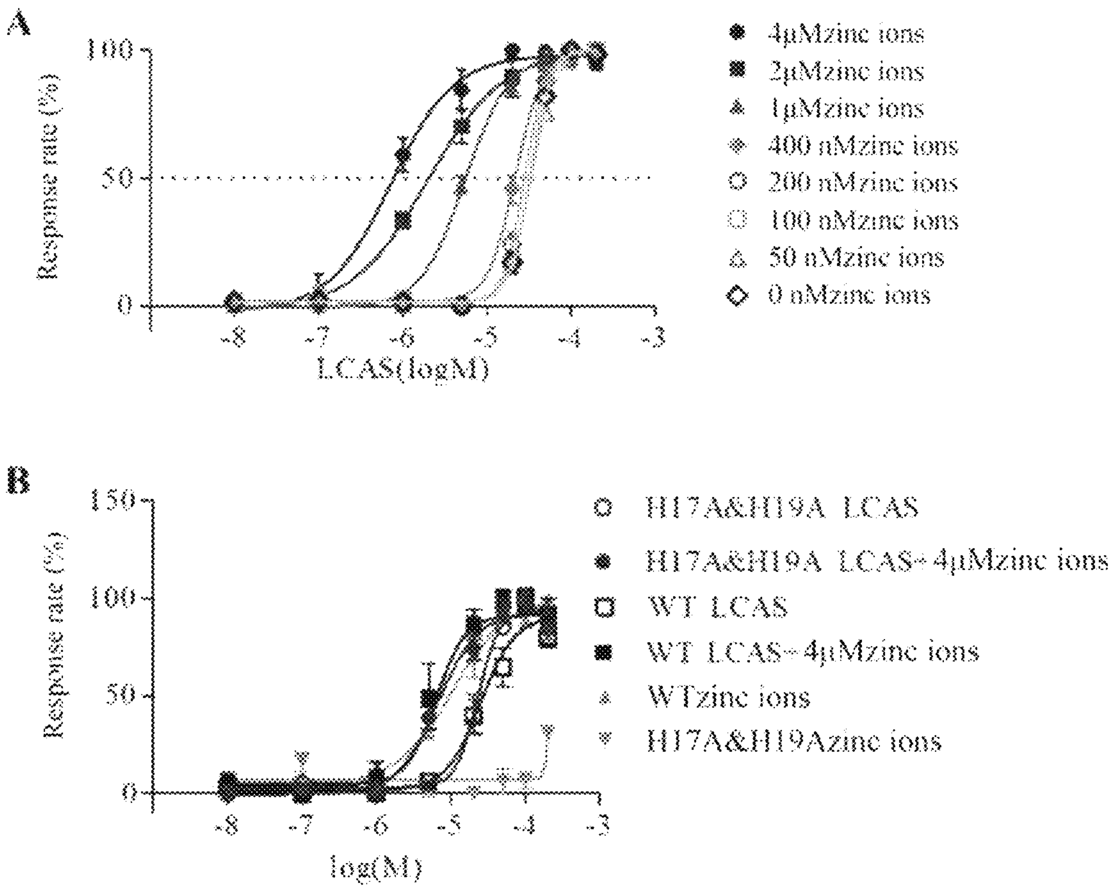
FIG. 4A shows dose curves of LCAS for activating GPR39 receptors on m39-20 cell lines after adding different concentrations of zinc ions.
FIG. 4B shows dose curves of LCAS for activating mutants H17A and H19A of GPR39 receptors on m39-20 cell lines.

HEK293T cells were seeded in a PDL-coated 96-well plate (coring Co.) at an appropriate density (about $3\times10^4$ cells/well) and cultured under conditions of 37° C. and 5% $CO_2$. 24 h after seeding, when the cell density reached 60%-70%, Lipofectamine 3000 (Invitrogen) was used for transfection, in which the concentration of plasmid transfection was 50 ng per well. 24 h after transfection, the concentration for 50% of maximal effect (EC50) of LCAS to activate the responding receptors on cells transiently transfected with wild-type (WT) GPR39 and its mutants was detected by the method of Example 3, with the results shown in Table 4 and FIG. 4B below. The results show that: 1) the activation of GPR39 by bile acids and derivatives thereof is independent of the previously reported zinc ion binding sites H17 and H19, and the activation mechanism of GPR39 is different from that of zinc ions. 2) Zinc ions have strong positive allosteric modulation effect on the activation of mutants H17A and H19A of GPR39 by LCAS.

TABLE 4

| | EC50 (μM) | |
|---|---|---|
| Name | H17A and H19A | WT |
| LCAS | 24 ± 0.8 | 33.1 ± 5.1 |
| LCAS + 4 μM zinc ions | 8.7 ± 0.8 | 5.2 ± 0.7 |
| Zinc ions | >100 | 12 ± 5.3 |

Example 6 Comparison of Bile Acids and Known GPR39 Agonists

Figure 6:
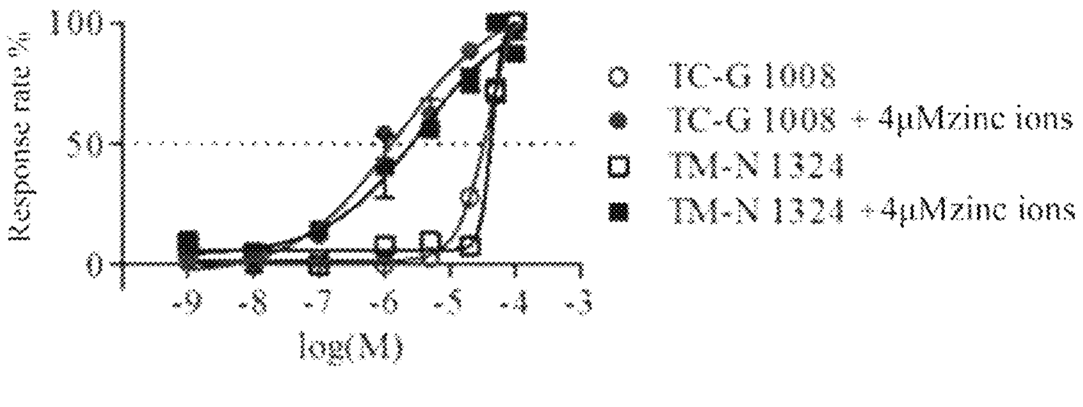
FIG. 6 shows dose curves of GPR39 agonists, TG-G 1008 and TM-N 1324, for activating GPR39 receptors on m39-20 cell lines.

According to the method of Example 3, the concentrations for 50% of maximal effect (EC50) of known GPR39 agonists TC-G 1008 (cat. no 5355, Tocris Co.) and TM-N 1324 (cat. no 6325, Tocris Co.) to activate GPR39 on m39-20 cell lines were detected, with the detection results shown in Table 5 below, and the dose curve shown in FIG. 6. By comparing with the detection results in Example 3, it may be known that in the presence of 4 μM zinc ions, the EC50 value of the bile acid derivative LCAS is 0.88±0.16 μM, which is less than the EC50 value (1.5 μM) of TC-G 1008 under the same conditions, and also less than the EC50 value (3.5 μM) of TM-N 1324 under the same conditions, indicating that the efficacy of LCAS to activate GPR39 is superior to that of the known GPR39 agonists TC-G 1008 and TM-N 1324.

TABLE 5

| | EC50 (μM) | |
|---|---|---|
| Name | Only agonist | Agonist + 4 μM zinc ions |
| TG-G 1008 | 39 | 1.5 |
| TM-N 1324 | 42.9 | 3.5 |

Example 7 Calcium Imaging of Known GPR39 Activation Site Mutants by Bile Acids GPR39 mutants E90A, F115A, E116A and D330A were firstly constructed according to the method of Example 5. The sequences of the forward and reverse primers used in the construction of each mutant are shown in Table 6 below, respectively.

TABLE 6

| Name | SEQ ID NO |
|---|---|
| m39-E90A-F | 3 |
| m39-E90A-R | 4 |
| m39-F115A-F | 5 |
| m39-F115A-R | 6 |
| m39-E116A-F | 7 |
| m39-E116A-R | 8 |
| m39-D330A-F | 9 |
| m39-D330A-R | 10 |

Figure 7:
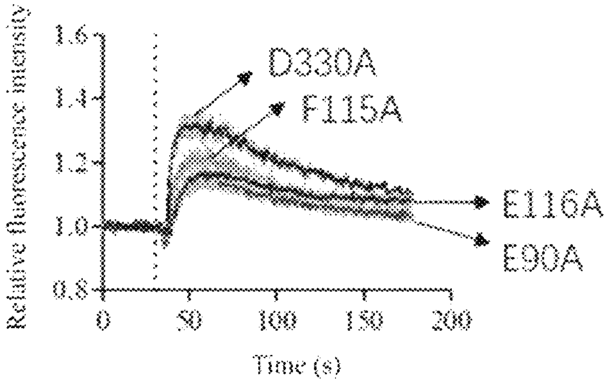
FIG. 7 shows the results of calcium imaging experiments on the activation of GPR39 receptor activation site mutants E90A, F115A, E116A and D330A by LCAS on m39-20 cell lines.

After then, the calcium imaging experiments of LCAS-activated GPR39 activation site mutants E90A, F115A, E116A and D330A were conducted on Lipofectamine 3000 transiently transfected cell systems according to the method of Example 5.2, with the detection results shown in FIG. 7. The results show that: 1) GPR39 activation site mutants E90A, F115A, E116A and D330A may all be activated by LCAS; 2) the activation of GPR39 by bile acids is independent of the known agonist binding sites.

Example 8 Calcium Imaging of Ghrelin Receptor Family by Bile Acids

GPR39 is one of G protein-coupled receptors belonging to the Ghrelin family, which has totally 7 members, including, in addition to GPR39, Ghrelin receptor (GHSR, NP_940799.1), Motilin receptor (MLNR, NP_001498.1), Neuromedin-U receptor 1 (NMUR1, NP_006047.3), Neuromedin-U receptor 2 (NMUR2, NP_064552.3), Neurotensin receptor 1 (NTSR1, NP_002522.2) and Neurotensin receptor 2 (NTSR2, NP_036476.2).

Figure 8:
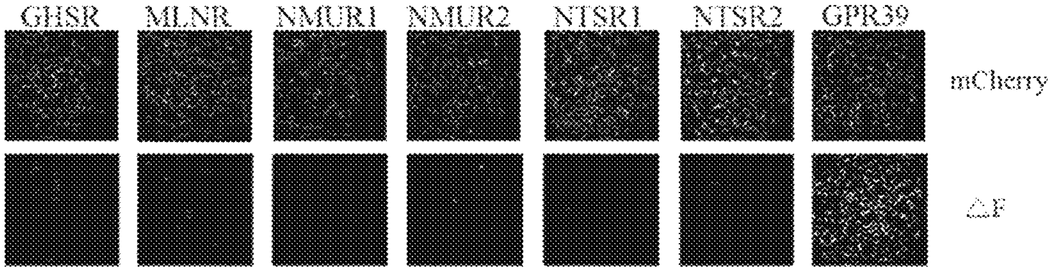
FIG. 8 shows the results of calcium imaging experiments on the activation of six receptors of Ghrelin family by LCAS.

According to the transient transfection method of Example 5.2, the 6 receptors of Ghrelin family except GPR39 were overexpressed in HEK293T cells respectively (the expression vectors for these 6 receptors came from the research group of Rao Yi, Peking University), and calcium dye was incubated. An inverted laser confocal microscope (leica Co.) was used to detect the activation of the 6 receptors of Ghrelin family by LCAS. The specific operations were as below: placing the cells to be detected on the microscope stage, detecting the fluorescence signal value of the calcium dye Fluo8 with the 488 nm channel, and detecting the fluorescence signal value of mCherry with the 543 nm channel. The detection results are shown in FIG. 8. All receptors fused to express the red fluorescence protein mCherry, and the expression of receptors was determined by detecting the red fluorescence emitted from mCherry. The results show that only GPR39 may be activated by 200 μM LCAS, and all the other 6 receptors of Ghrelin family cannot be activated by 200 μM LCAS.

Figure 10:
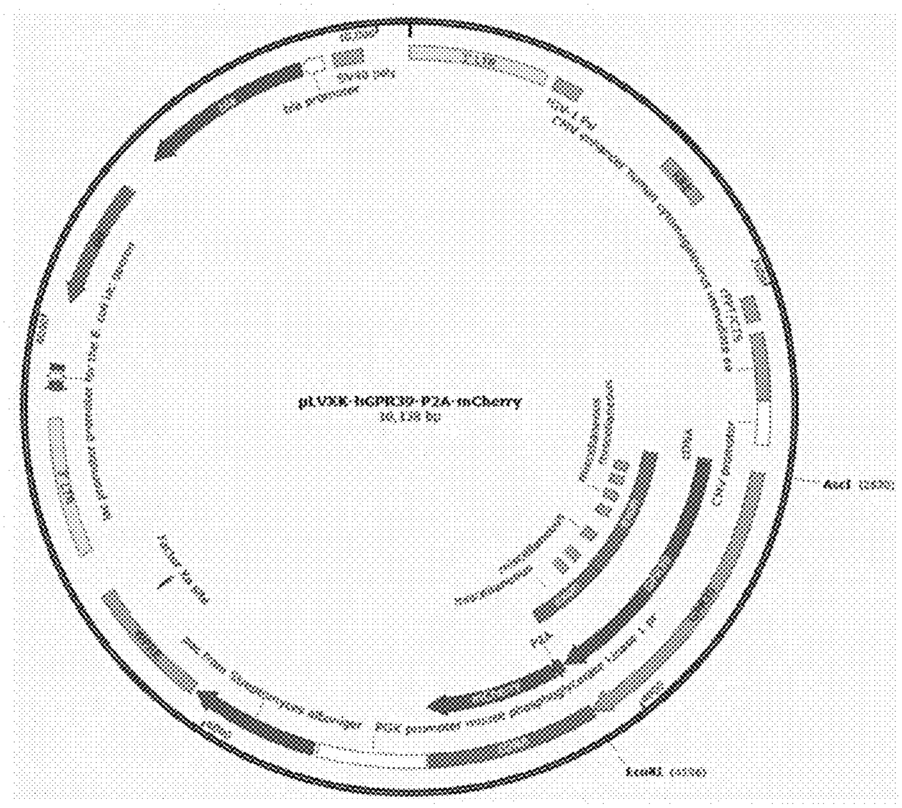
FIG. 10 shows a map of a lentiviral vector PLVXK-hGPR39-P2A-mCherry.

Example 9 Activation of Cell Line Human GPR39-2 Stably Expressing Human GPR39 Gene by Bile Acids The human GPR39 cDNA vector was purchased from WZ Biosciences Inc., Shandong. It was cloned onto a lentiviral vector PLVXK-hGPR39-P2A-mCherry (FIG. 10) through PCR amplification using primers hGPR39-F (which sequence was shown as set forth in SEQshown as set forth in SEQ ID NO: 15) and hGPR39-R (which sequence was shown as set forth in SEQ shown as set forth in SEQ ID NO: 16), in which the sequence of the target gene human GPR39 cDNA was shown as set forth in SEQ shown as set forth in SEQ ID NO: 14. A cell line human GPR39-2 stably expressing human GPR39 gene was constructed according to the method of Example 1.

The calcium imaging of human GPR39-2 cell lines, the concentration for 50% of maximal effect (EC50) for the activation of GPR39 receptors, as well as the modulation of zinc ions on the activation of human GPR39 receptors by LCAS, TLCAS, GLCAS were respectively detected according to the methods of Example 2 and Example 3.

Figure 9:
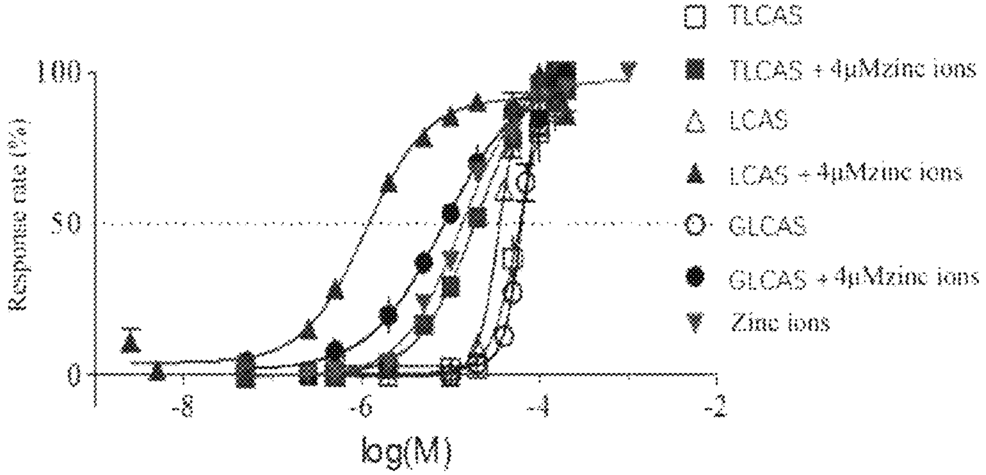
FIG. 9 shows the results of calcium imaging experiments on human GPR39-2 cell lines by LCAS, TLCAS, GLCAS.

The detection results are shown in Table 7 below and FIG. 9, from which it is indicated that LCAS, TLCAS, GLCAS are all capable of inducing intracellular calcium signal response of human GPR39-2, and have a concentration-dependent effect, and zinc ions also have positive allosteric modulation effect on human GPR39 receptors.

TABLE 7

| | EC50 (μM) | |
|---|---|---|
| Name | Only agonist | Agonist + 4 μM zinc ions |
| LCAS | 42.4 ± 3.9 | 0.97 ± 0.3 |
| TLCAS | 69.4 ± 5 | 9.6 ± 6.3 |
| GLCAS | 66.8 ± 8.8 | 8.7 ± 1.1 |
| Zinc ions | | 12 ± 2.8 |

The foregoing detailed description is provided by way of explanation and examples, and is not intended to limit the scope of the appended claims. Various changes of the embodiments currently enumerated in this application will be apparent to those of ordinary skills in the art, and are reserved within the scope of the appended claims and their equivalents.

The invention claimed is:

1. A method for activating G protein coupled receptor 39 (GPR39) in a subject in need thereof, the method comprising administering a zinc ion and at least one of a bile acid or bile acid derivative to the subject in an amount sufficient to activate GPR39, wherein the bile acid derivative is at least one selected from the group consisting of CA (cholic acid), chenodeoxycholic acid (CDCA), deoxycholic acid (DCA), glycolithocholic acid (GLCA), lithocholic acid 3-sulfate (LCAS), taurolithocholic acid 3-sulfate (TLCAS), glycolithocholic acid 3-sulfate (GLCAS), taurodeoxycholic acid (TDCA), glycodeoxycholic acid (GDCA), deoxycholic acid 3-sulfate (DCAS), ursodeoxycholic acid 3-sulfate (UDCAS), glycochenodeoxycholic acid (GCDCA), or a pharmaceutically acceptable salt thereof.

2. The method according to claim 1, wherein the subject has a gastrointestinal disease.

3. The method according to claim 2, wherein the gastrointestinal disease is at least one selected from the group consisting of functional dyspepsia, diabetic gastroparesis, gastric spasm, irritable bowel syndrome, diarrhea, and chronic constipation.

4. The method according to claim 1, wherein the concentration of the zinc ions is 10 nM to 10 μM.

5. The method according to claim 1, wherein the GPR39 is a human GPR39 or a mouse GPR39.

6. A method for activating G protein coupled receptor 39 (GPR39) in a subject in need thereof, the method comprising administering a bile acid derivative to the subject in an amount sufficient to activate GPR39, wherein the bile acid derivative is at least one selected from the group consisting of lithocholic acid 3-sulfate (LCAS), taurolithocholic acid 3-sulfate (TLCAS) and glycolithocholic acid 3-sulfate (GLCAS), or a pharmaceutically acceptable salt thereof.

7. The method according to claim 6, wherein the subject has a gastrointestinal disease.

8. The method according to claim 7, wherein the gastrointestinal disease is at least one selected from the group consisting of functional dyspepsia, diabetic gastroparesis, gastric spasm, irritable bowel syndrome, diarrhea, and chronic constipation.

9. The method according to claim 6, wherein the GPR39 is a human GPR39 or a mouse GPR39.

* * * * *